United States Patent [19]
Szabo

[11] Patent Number: 5,885,282
[45] Date of Patent: Mar. 23, 1999

[54] APPARATUS FOR TREATMENT OF FRACTURE AND MALUNION OF THE DISTAL RADIUS

[75] Inventor: Robert M. Szabo, Sacramento, Calif.

[73] Assignee: The Regents of the University of California, Oakland, Calif.

[21] Appl. No.: 853,710

[22] Filed: May 9, 1997

[51] Int. Cl.⁶ .................................................. A61B 17/56
[52] U.S. Cl. .............................................. 606/56; 606/57
[58] Field of Search ................................ 606/56, 57, 58, 606/54, 55, 59

[56] References Cited

U.S. PATENT DOCUMENTS

| | | |
|---|---|---|
| 4,535,763 | 8/1985 | Jaquet . |
| 5,074,866 | 12/1991 | Sherman et al. . |
| 5,372,597 | 12/1994 | Hotchkiss et al. . |
| 5,496,319 | 3/1996 | Allard et al. . |

FOREIGN PATENT DOCUMENTS

| | | |
|---|---|---|
| 745511 | 7/1980 | U.S.S.R. . |
| 354-378 | 8/1981 | U.S.S.R. . |
| 1237-189-A | 6/1986 | U.S.S.R. . |
| 1324-662-A | 7/1987 | U.S.S.R. . |
| 15114-359-A | 10/1989 | U.S.S.R. . |

*Primary Examiner*—Guy V. Tucker
*Attorney, Agent, or Firm*—John P. O'Banion

[57] ABSTRACT

An external fixation apparatus for applying force against a single isolated plane of deformity in the distal radius for fracture treatment, and which can be used to avoid the need for a bone graft to correct a distal radius malunion. A pair of laterally spaced-apart circular rings are coupled by three rods extending between the rings. Z-shaped brackets are used to offset each of the rods distal to the distal ring, and each rod is pivotally coupled to a Z-shaped bracket by a ball joint. One of the rods is also coupled to a gear mechanism and functions as a pushrod that provides for adjustment of the spacing between the rings along the axis of the pushrod. Each ring carries a radius fixation mechanism, and an optional metacarpal fixation mechanism can be attached to the distal side of the distal ring. An optional ulnar fixation mechanism can also be attached to the proximal ring.

15 Claims, 2 Drawing Sheets

APPARATUS FOR TREATMENT OF FRACTURE AND MALUNION OF THE DISTAL RADIUS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to treating bone fractures, and more particularly to an external fixation apparatus for treatment of fractures and malunions of the distal radius which eliminates the need for bone grafting.

2. Description of the Background Art

External fixation devices are well known in the field of orthopedic medicine, and such devices are widely used to support and align a fractured bone to facilitate healing. External fixators commonly include a frame made from interconnected bars and full or partial rings having a number of holes, where the rings fit partially around the bone, or completely surround the bone. Additionally, single rings can be used or multiple spaced-apart rings can be used. The devices are then secured to the bone using transfixating wires or pins and/or non-transfixating pins. Transfixating wires and pins pass laterally through the bone and are typically connected at opposite ends to the frame, whereas non-transfixating pins are introduced into the bone without completely transversing it. Once the pins or wires are inserted in the bones and tissue, small adjustment to the alignment to the frame with respect to the bone are typically made by removing, realigning and reattaching components to the bone.

A common problem with the majority of external fixation systems used for the distal radius is that they are only capable of maintaining a reduction that is obtained manually. Such systems apply ligamentaxis in a longitudinal fashion without concern for the three dimensionality of the fracture deformity. One device that is available, known as the Agree Wrist Jack, has attempted to solve this problem by applying ligamentaxis in several planes, and the technique is referred to as "multiplanar ligamentaxis" in the medical field. This device, however, tries to achieve reduction in a stepwise fashion; that is, a deformity is corrected sequentially in one plane at time. Unfortunately, however, correcting one plane of deformity creates a block to correcting the second plane of deformity due to the ligamentous anatomy. While the Agee Wrist Jack is the current state of the art in distal radius fracture fixation, it suffers from the lack of appreciation that a fracture deformity is three dimensional and exists in only one plane.

In an attempt to solve this problem, devices have been developed to direct the force against the single isolated plane of deformity. For example, the Ilizarov methodology of fracture fixation employs a huge assortment of rings and pieces of equipment that look very similar to an erector set, and use of the equipment requires special training. The frame is fashioned from the rings and rods using nuts and bolts, with complicated assembly being required each time that a frame is set up for a particular patient. In addition, the device requires complicated disassembly and, in effect, rebuilding of the frame configuration to make periodic adjustment. Most surgeons who treat fractures are intimidated by the complexity of such equipment.

In addition, the current state of the art for correcting distal radius malunions is surgical osteotomy of the bone followed by bone grafting with plate fixation. This requires harvesting the bone from the iliac crest, thus creating more morbidity. It also leaves a plate and screws in a person which can cause future problems. While the Ilizarov methodology can be used to avoid a bone graft, the equipment is very complex as described above.

Therefore, there is a need for an external fixation device that can be used for both fracture treatment and malunion treatment of the distal radius in the forearm, that does not require complicated assembly and disassembly, and that will direct the applied force against the single isolated plane of deformity. The present invention satisfies those needs, as well as others, and overcomes the deficiencies in currently available technology.

BRIEF SUMMARY OF THE INVENTION

The present invention generally pertains to an apparatus that directs applied force against a single isolated plane of deformity for fracture treatment, and which can be used to avoid the need for a bone graft to correct a distal radius malunion. By way of example, and not of limitation, the invention comprises a pair of laterally spaced-apart circular rings that are coupled by three linking mechanisms extending between the rings. The linking mechanisms generally comprise rods with ball joints adjacent to one end. The two rings are of different sizes, the distal ring being smaller in diameter than the proximal ring. Small "Z"-shaped brackets are used to offset each of the rods distally to the distal ring, and each rod is pivotally coupled to a "Z"-shaped bracket by a ball joint. One of the rods is also coupled to a gear mechanism that so as to function as a pushrod. By adjusting the gear mechanism, the push rod can be effectively lengthened or shortened in relation to the distal ring, thereby changing the spacing between the rings along the axis of the pushrod. Thus, this combination of elements allows for adjustment of the relative position of the two rings about a single axis so that the axis of rotation can be set at the joint level of the wrist for correction along a single plane of deformity.

Each ring carries a radius fixation mechanism that carries a half pin for insertion into the radius. In addition, an optional metacarpal fixation mechanism can be attached to the distal side of the distal ring. The metacarpal fixation mechanism, which would generally be used only in the case of fractures and not where malunions are being treated, carries a pair half pins that can be inserted into the second metacarpal. A pushrod and gear mechanism holds the half pins away from the distal ring and allows for adjustment of the extension position of the half pins in relation to the distal ring. Furthermore, an optional ulnar fixation mechanism carrying a half pin for insertion into the ulnar can be attached to the proximal ring. Additional fixation pins are provided for attachment to the proximal and distal rings for additional control of fracture fragments. Furthermore, smooth tension wires can be attached to the rings as desired.

An object of the invention is to provide an external distal radius fixation apparatus that applies force along a single isolated plane of deformity.

Another object of the invention is to provide an external distal radius fixation apparatus that can be used for both fracture treatment and malunion treatment of the distal radius in the forearm.

Another object of the invention is to provide an external fixation apparatus that does not require complicated assembly and disassembly.

Another object of the invention is to provide an external fixation apparatus that can support the second metacarpal.

Another object of the invention is to provide an external radius fixation apparatus that can support the ulnar.

Another object of the invention is to provide an external radius fixation apparatus that can eliminate the need for bone grafts to correct malunions in the wrist.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
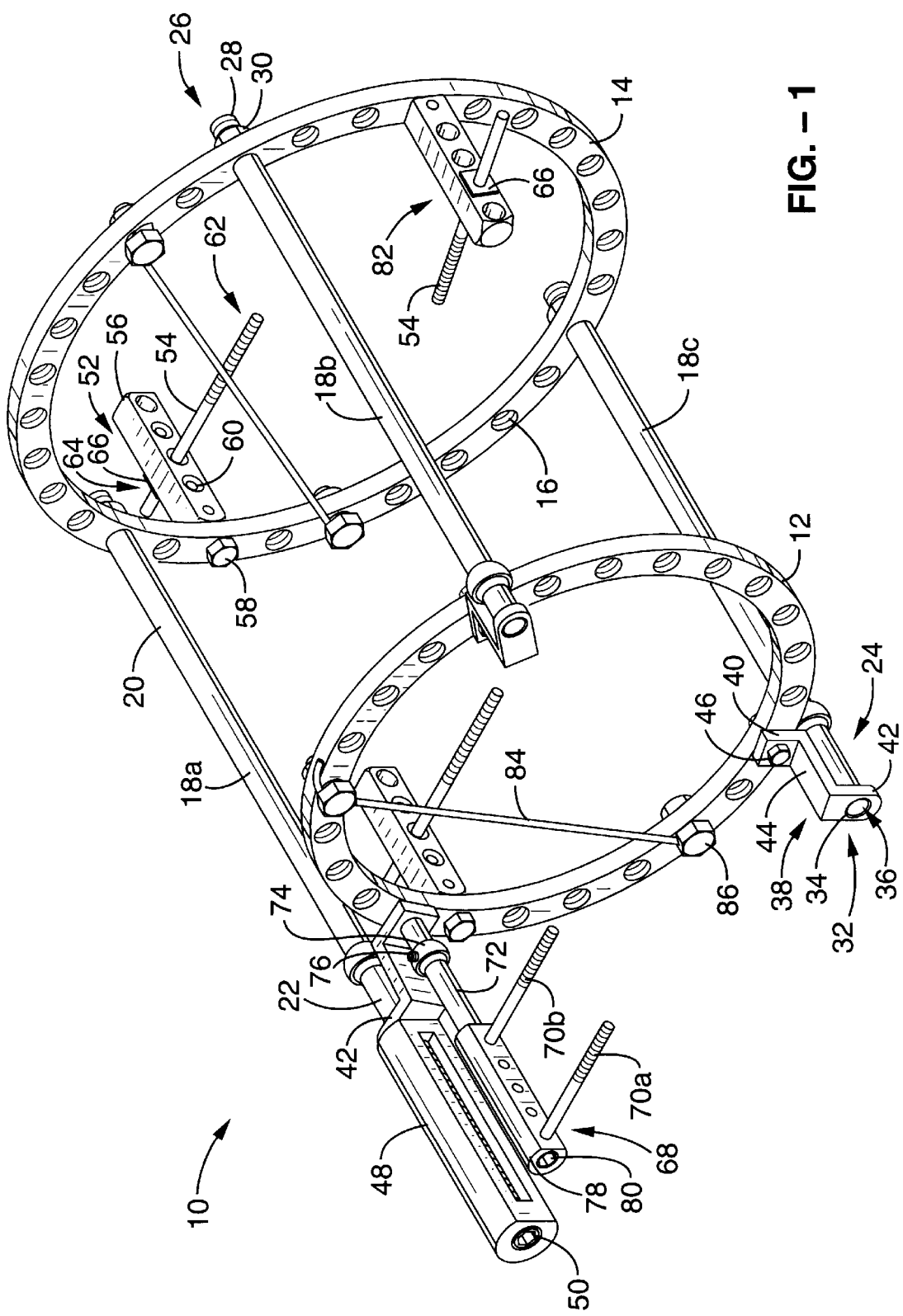
FIG. 1 is a perspective view of a fixation apparatus in accordance with the present invention.
Figure 2:
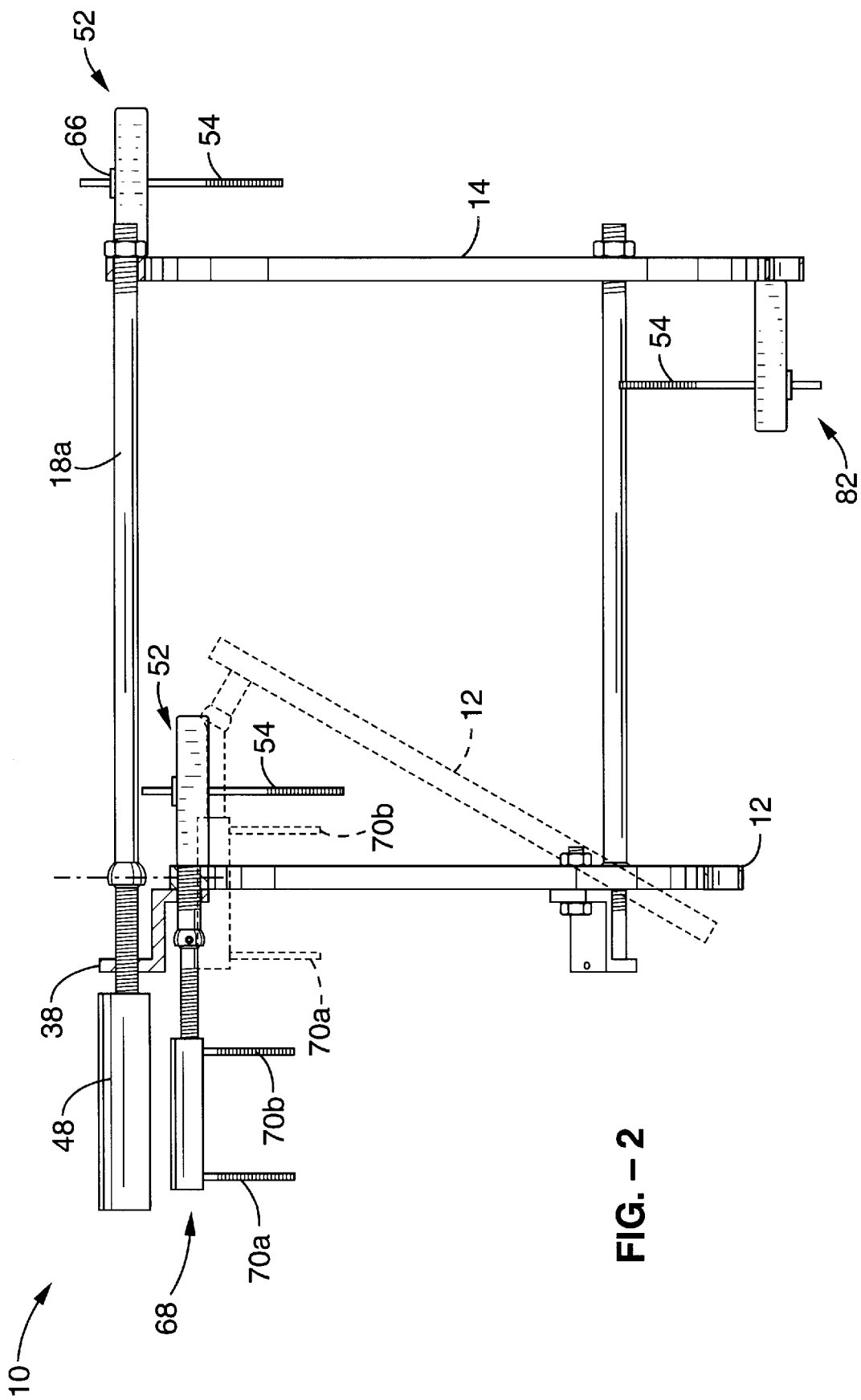
FIG. 2 is a top plan view of the apparatus shown in FIG. 1 diagrammatically showing the manner in which the fixation rings can be adjusted in a single isolated plane of deformity.

Referring more specifically to the drawings, for illustrative purposes the present invention is embodied in the apparatus 10 generally shown in FIG. 1 and FIG. 2, where like reference numerals denote like parts. It will be appreciated that the apparatus may vary as to configuration and as to details of the parts without departing from the basic concepts as disclosed herein.

Referring first to FIG. 1, the invention comprises a first, distally positioned (toward wrist) circular ring 12 and a second, proximally positioned circular ring 14. Each ring includes a plurality of threaded receptacles 16 extending between the faces of the rings and positioned around the circumference of the rings. The two rings are of different sizes, with the distal ring 12 being smaller in diameter than the proximal ring 14. Rings 12, 14 are laterally spaced-apart and coupled together by three linking mechanisms 18a, 18b, 18c extending between the rings. The linking mechanisms generally comprise rod members 20 with ball joint members 22 positioned adjacent to the distal ends 24 of the linking mechanisms. The proximal end 26 of each rod member 20 preferably contains threads 28 which mate with receptacles 16 in proximal ring 14. Optionally, a nut 30 can be threaded over the ends of the rods to ensure a locked engagement. The distal end 32 of each ball joint member 22 also preferably contains threads 34 which mate with threaded receptacles 36 in small "Z-shaped" brackets 38 that are used to used to offset each of the linking mechanisms distally to the distal ring 12 and to position the distal ends of the linking mechanisms radially outward from the circumference of distal ring 12.

Each of the Z-shaped brackets 38 includes a first leg 40, a second leg 42 and a body member 44 extending between the legs. The first leg 40 is coupled to distal ring 12 in such an orientation that second leg 42 is positioned distally to distal ring 12 and radially outward from the circumference of distal ring 12. Coupling is preferably by means of a bolt 44 and nut 46 or like fasteners. Alternatively, the first leg 40 could be spot welded or fixed to distal ring 12, but it is preferable to use a reversible coupling mechanism to allow repositioning of the Z-shaped brackets if desired. The linking mechanisms are coupled to the second leg 42 of the Z-shaped brackets 38 as shown and, because the diameter of distal ring 12 is less than the diameter of proximal ring 14, the linking mechanisms are aligned generally parallel in relation to each other. It will be appreciated that the linking mechanisms can be made in different lengths, depending upon the particular need, or could be made in such a manner that extension links can be added. It will also be appreciated that the diameter of the distal and proximal rings can vary.

Note that linking mechanism 18a is coupled to a gear mechanism 48 that so as to function as a pushrod. Here, gear mechanism 48 is coupled to the second leg 42 of the Z-shaped bracket 38 and the threaded end of the linking mechanism extends into the gear mechanism 48. By turning an adjusting screw 50 or the like attached to the end of the pushrod, the pushrod can be effectively lengthened or shortened in relation to distal ring 12, thereby changing the spacing between the rings along the axis of the pushrod. The gear mechanism can be a simple thread arrangement as shown, or a more complicated worm gear mechanism or the like if desired. By adjusting the pushrod, the relative position of the two rings can be adjusted about a single axis so that the axis of rotation can be set at the joint level of the wrist for correction along a single plane of deformity.

Each ring carries a radius fixation mechanism 52 that in turn carries a conventional half pin 54 for insertion into the distal radius of the arm. The fixation mechanism 52 generally comprises an elongated base 56 that is coupled at one end to the ring by means of a bolt 58 extending into threads (not shown) in the end of the base 56. Base 56 also includes a plurality of receptacles 60 for receiving the half pin 54 and allowing for adjustment of the position of the half pin in relation to the ring. The half pin has a threaded end 62 for insertion in to the bone, and a smooth end 64 for insertion into a receptacle 58. If desired, a friction pad 66 can be used to prevent half pin 54 from sliding in receptacle 58.

In addition, an optional metacarpal fixation mechanism 68 can be attached to the distal side of the distal ring 12. The metacarpal fixation mechanism 68, which would generally be used only in the case of fractures and not where malunions are being treated, carries a pair half pins 70a, 70b that can be inserted into the second metacarpal of the hand. Metacarpal fixation mechanism 68 is preferably pivotally coupled to the distal ring 12 using a link rod 72 and ball joint 74 as shown, and can be locked into a pivotal position using a set screw 76 or the like. Link rod 72 is threaded into a base member 78 so that the distal extension position of the half pins in relation to distal ring 12 can be adjusted using an adjustment screw 80 in the same or similar to the operation of gear mechanism 48.

Furthermore, an optional ulnar fixation mechanism 82 carrying a half pin for insertion into the ulnar can be attached to the proximal ring as shown. The ulnar fixation mechanism 82 would be of the same or similar configuration as the radius fixation mechanism 58. Additional fixation mechanisms and pin can be provided for attachment to the proximal and distal rings for additional control of fracture fragments. In addition, smooth tension wires 84 can be attached to and spanned across the rings using conventional nut and bolt fasteners 86 as desired. Referring also to FIG. 2, it can be seen that adjustment of pushrod 18a will change relative position of the proximal and distal rings by directing applied force against a single isolated plane of deformity.

Accordingly, it will be seen that this invention provides an external fixation device that can be used for both fracture treatment and malunion treatment of the distal radius in the arm, that does not require complicated assembly and disassembly, and that will direct the applied force against the single isolated plane of deformity. The apparatus can be fabricated from commonly available materials suitable for medical use, including stainless steel, titanium, and carbon fiber. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for treatment of bone fractures and malunions, comprising:
   (a) a pair of spaced-apart rings;
   (b) a plurality of connecting rods, each said connecting rod having first and second ends, each said connecting rod including a pivotal coupling between said first and second ends;
   (c) a plurality of z-shaped brackets, each said bracket having a first leg, a second leg, and a body member between said legs, said first leg of each said bracket coupled to a first of said rings;
   (d) said first end of each said connecting rod coupled to said second leg of one of said z-shaped brackets, said second end of each said connecting rod coupled to a second of said rings;
   (e) means for adjusting the spacing between said rings along the lengthwise axis of at least one of said connecting rods; and
   (f) means for coupling each of said rings to a bone.

2. An apparatus as recited in claim 1, wherein said first of said rings is positioned distal to said second of said rings, and wherein said second leg of each said bracket is positioned distal to said first of said rings.

3. An apparatus as recited in claim 1, wherein said first of said rings has a diameter less than said second of said rings.

4. An apparatus as recited in claim 3, wherein said first ring has a circumference and wherein said second leg of each said bracket is positioned radially outward from the circumference of said first of said rings.

5. An apparatus as recited in claim 1, further comprising metacarpal fixation means for coupling at least one of said rings to a metacarpal.

6. An apparatus as recited in claim 1, further comprising ulnar fixation means for coupling at least one of said rings to an ulnar.

7. An external fixation apparatus for treatment of bone fractures and malunions, comprising:
   (a) a first circular ring;
   (b) a second circular ring spaced apart from said first circular ring, said second ring having a diameter greater than the diameter of said first ring;
   (c) a plurality of connecting rods, each said connecting rod having first and second ends, each said connecting rod including a pivotal coupling between said first and second ends;
   (d) a plurality of z-shaped brackets, each said bracket having a first leg, a second leg, and a body member between said legs, said first leg of each said z-shaped bracket coupled to said first ring;
   (e) wherein said first end of each said connecting rod is coupled to said second leg of one of said z-shaped brackets, wherein said first ring has a circumference and said first end of each said connecting rod is positioned radially outward from the circumference of said first ring, and wherein said second end of each said connecting rod is coupled to said second ring;
   (f) means for adjusting the spacing between said first and second rings along the lengthwise axis of at least one of said connecting rods; and
   (g) means for coupling each of said rings to a bone.

8. An apparatus as recited in claim 7, wherein said first ring is positioned distal to said second ring and wherein second leg of each said bracket is positioned distal of said first ring.

9. An apparatus as recited in claim 7, further comprising metacarpal fixation means for coupling at least one of said rings to a metacarpal.

10. An apparatus as recited in claim 7, further comprising ulnar fixation means for coupling at least one of said rings to an ulnar.

11. An external fixation apparatus for treatment of a bone fracture or malunion, comprising:
    (a) a distal ring, said distal ring having a circumference;
    (b) a proximal ring, said proximal ring having a diameter greater than the diameter of said distal ring;
    (c) a plurality of connecting rods, each said connecting rod having first and second ends, each said connecting rod including a pivotal coupling between said first and second ends positioned adjacent said first end;
    (d) a plurality of z-shaped brackets, each said bracket having a first leg, a second leg, and a body member between said legs, said first leg of each said z-shaped bracket coupled to said distal ring wherein said each said second leg is positioned distal of said distal ring;
    (e) said first end of each said connecting rod coupled to said second leg of said z-shaped bracket wherein said first end of each said connecting rod is positioned radially outward from the circumference of said distal ring, said second end of each said rod coupled to said proximal ring;
    (f) means for adjusting the spacing between said first and second rings along the lengthwise axis of at least one of said connecting rods; and
    (g) means for coupling said proximal and said distal rings to a bone.

12. An apparatus as recited in claim 11, further comprising metacarpal fixation means for coupling at least one of said rings to a metacarpal.

13. An apparatus as recited in claim 11, further comprising ulnar fixation means for coupling at least one of said rings to an ulnar.

14. An apparatus for treatment of bone fractures and malunions, comprising:
    (a) a pair of spaced-apart rings, wherein said first of said rings has a diameter less than said second of said rings;
    (b) a plurality of connecting rods, each said connecting rod having first and second ends, each said connecting rod including a pivotal coupling between said first and second ends;
    (c) a plurality of brackets, each said bracket having a first leg, a second leg, and a body member between said legs, said first leg of each said bracket coupled to a first of said rings;

(d) said first end of each said connecting rod coupled to said second leg of one of said brackets, said second end of each said connecting rod coupled to a second of said rings;

(e) means for adjusting the spacing between said rings along the lengthwise axis of at least one of said connecting rods; and (f) means for coupling each of said rings to a bone.

15. An apparatus as recited in claim 14, wherein said first ring has a circumference and wherein said second leg of each said bracket is positioned radially outward from the circumference of said first of said rings.

* * * * *